United States Patent [19]

Ranke et al.

[11] Patent Number: 4,690,812

[45] Date of Patent: Sep. 1, 1987

[54] INTEGRATED PRODUCTION OF AMMONIA AND UREA

[75] Inventors: Gerhard Ranke, Poecking; Ulrich Schrader, Munich, both of Fed. Rep. of Germany

[73] Assignee: Linde Aktiengesellschaft, Wiesbaden, Fed. Rep. of Germany

[21] Appl. No.: 692,563

[22] Filed: Jan. 18, 1985

[30] Foreign Application Priority Data

Jan. 19, 1984 [DE] Fed. Rep. of Germany ....... 3401779

[51] Int. Cl.$^4$ .............................................. C01C 1/04
[52] U.S. Cl. ....................................... 423/359; 564/69
[58] Field of Search ..................... 423/359; 55/47, 48, 55/68; 564/69

[56] References Cited

U.S. PATENT DOCUMENTS

| | | | |
|---|---|---|---|
| 2,649,166 | 8/1953 | Porter et al. | 55/68 |
| 2,926,751 | 3/1960 | Kohl et al. | 55/68 |
| 2,926,753 | 3/1960 | Kohl et al. | 55/68 |
| 3,196,596 | 7/1965 | Miller | 55/68 |
| 3,242,640 | 3/1966 | Woertz | 55/68 |
| 3,248,855 | 5/1966 | Hartmann | 55/68 |
| 3,640,052 | 2/1972 | Konoki et al. | 55/68 |
| 3,880,615 | 4/1975 | Grunewald et al. | 55/68 |
| 4,291,006 | 9/1981 | Pagani et al. | 423/359 |

FOREIGN PATENT DOCUMENTS 3239605.8 4/1984 Fed. Rep. of Germany .

OTHER PUBLICATIONS

Strelzoff, *Technology and Manufacture of Ammonia*, John Wiley & Sons (1981), pp. 251–254.

*Primary Examiner*—John Doll
*Assistant Examiner*—Wayne A. Langel
*Attorney, Agent, or Firm*—Millen & White

[57] ABSTRACT

The combined production of ammonia and urea by the reaction of gases containing hydrocarbons with steam is conducted by using a steam reformer, downstream secondary reformer, and shift converter. The ammonia synthesis gas (hydrogen, nitrogen and carbon dioxide) is subjected to a high pressure scrubbing step with a physical solvent, to remove the acid impurities, especially $CO_2$. The pressure on the loaded solvent is reduced to a first intermediate pressure for degasing of the coabsorbed inerts and then to a second intermediate pressure for removal of the bulk of the absorbed $CO_2$, which is then used for urea synthesis. To remove residual $CO_2$, the solvent is stripped with air and the resultant air stream containing the stripped residual $CO_2$ is fed to the secondary reformer.

5 Claims, 2 Drawing Figures

INTEGRATED PRODUCTION OF AMMONIA AND UREA

CROSS-REFERENCE TO RELATED APPLICATION

This application is related to a concurrently filed application entitled "Separation of $CO_2$ from Gaseous Mixtures", Ser. No. 692,556 insofar as both applications relate to the removal of residual $CO_2$ from a scrubbing solution.

BACKGROUND OF THE INVENTION

This invention relates to the separation of $CO_2$ from a scrubbing solution, and especially its application to the combined production of ammonia and urea.

In a more comprehensive aspect, this invention relates to the conversion of hydrocarbons to produce ammonia synthesis gas and $CO_2$, by using a conventional steam reformer, downstream secondary reformer, and shift converter. The resultant ammonia synthesis gas, consisting essentially of hydrogen, nitrogen and carbon dioxide, is subjected to a high pressure scrubbing step with a physical solvent to remove acid impurities, and especially $CO_2$ which is recovered from the loaded solvent. The regenerated solvent is recycled to the scrubbing step and the desorbed $CO_2$ is used for urea synthesis.

As is known, for example, from DE-PS No. 27 21 462, ammonia, which is produced from a mixture of hydrogen and nitrogen, is used as a reactant for the synthesis of urea. The ammonia synthesis gas, consisting essentially of hydrogen, nitrogen and carbon dioxide, produced conventionally, is scrubbed to remove carbon dioxide. The carbon dioxide is then desorbed at ambient pressure from the loaded scrubbing solution in a downstream regeneration column and then is used for urea synthesis.

The above method has the drawback that the carbon dioxide must then be compressed from atmospheric pressure to the urea synthesis pressure of about 160 bar, for which a very great expenditure of energy is required. To avoid this disadvantage, it has already been proposed in patent application No. P 32 39 605.8 to reduce the pressure on the loaded solvent to an intermediate value and to heat the pressure-reduced solvent to partially degas the $CO_2$. The degassed $CO_2$ consequently accumulates under pressure and, after being cooled, can be used for urea synthesis. The partially regenerated solvent is subjected to a final pressureless regeneration stage. There the solvent is either again heated in a reboiler for the removal of the residual $CO_2$ or freed of the residual $CO_2$ by use of a vacuum.

In the first mentioned variant, there is however, a high steam requirement for the reboiler for the heating of the solvent in two stages—partial degassing and removal of residual $CO_2$ as well for make-up heat exchange losses. In addition, cooling is required to compensate for the heating of the pumps and cooling of the crude gas. Linked with it is an expenditure for additional equipment such as a heat exchanger, reboiler, condenser with separator, and condensate pump.

Use of a vacuum on the other hand requires additional apparatus having a relatively high specific energy requirement. The attainable residual concentration of $CO_2$ in the solvent is determined by the suction pressure of the vacuum compressor. Thus, the crude gas cannot be purified as well in the scrubber. The $CO_2$ residual charge can be lowered by warming the solvent with waste heat, but then similar drawbacks occur as in the case of thermal regeneration.

SUMMARY OF THE INVENTION

An object of the invention is, therefore, to provide an improved process for the removal of $CO_2$ from a physical solvent.

Another object is to integrate the improved $CO_2$ removal system into a process requiring $CO_2$ and ammonia, and especially into a urea production process.

Still another object is to provide apparatus for the above processes.

Upon further study of the specification and appended claims, further objects and advantages of this invention will become apparent to those skilled in the art.

To attain these objects, the scrubbing solution is treated at regeneration final pressure with air as a stripping gas to remove $CO_2$. In the integrated process, stripping gas together with stripped residual $CO_2$ withdrawn from the stripping column is fed into a secondary reformer where residual methane is converted. In general, the stripping step reduces the $CO_2$ content in the scrubbing solution so far that a $CO_2$ content of 100 ppm $CO_2$ or less can be achieved*

*in the purified synthesis gas.

With this process, a thermal regeneration column is replaced with a stripping column. In this way the physical solvent can be desorbed of $CO_2$ without the use of steam or a vacuum. Furthermore, $CO_2$ can be removed in the scrubbing step to such an extent that methanation of the residual CO and $CO_2$ is economically justifiable. At the same time, all the $CO_2$ can be obtained as a product since the $CO_2$ fed to the secondary reformer is withdrawn from the latter without reaction and is scrubbed again in the scrubber. Therefore, a certain limited amount of $CO_2$ is indeed circulated but this amount is so small that it has no significant negative effect on the effectiveness of the process.

The loaded solvent is generally expanded in stages and then stripped with air. Therefore, for the final regeneration of the solvent, neither heat input nor heat exchange of loaded solvent against regenerated solvent is necessary.

The amount of air available for regeneration of the solvent according to the compreshensive aspect of the invention is determined by the air requirement of the secondary reformer. Thus, the regeneration final pressure is so selected that the amount of air necessary for the $CO_2$ stripping covers the requirement of the secondary reformer. If a natural gas containing $N_2$ is processed in the steam reformer, the air requirement for the secondary reformer is reduced since the nitrogen required for the ammonia synthesis gas is partially introduced by the feedstock. Therefore it is preferred that according to the invention the crude gas be compressed before scrubbing and then the $CO_2$ be scrubbed. Since physical scrubbing is involved, the $CO_2$ can be scrubbed with a smaller amount of solvent at increased pressure. At the same time, less air is needed for regeneration of the charged solvent. In the context of this aspect of the invention, by crude gas is meant the gas leaving the shift conversion, i.e. the $CO_2$ and water containing synthesis gas.

In this method, the $CO_2$ contained in the crude gas is indeed also compressed but in the expansion of the loaded solvent a large part of the $CO_2$ is recovered under a higher pressure, so that the total energy requirement for synthesis and $CO_2$ compression does not increase. An additional advantage of the process according to the invention is that $H_2$-rich gas can accumulate at an intermediate pressure and can be compressed with the crude gas compressor, whereby the need for a recycle compressor is eliminated.

The process according to the invention can be used with all physical solvents, as, for example, alcohols, ketones, N-methylpyrrolidone, polyethylene glycol ethers, dimethylformamide, glycols, butryolactone.

DETAILED DESCRIPTION OF FIGURES

Figure 1:
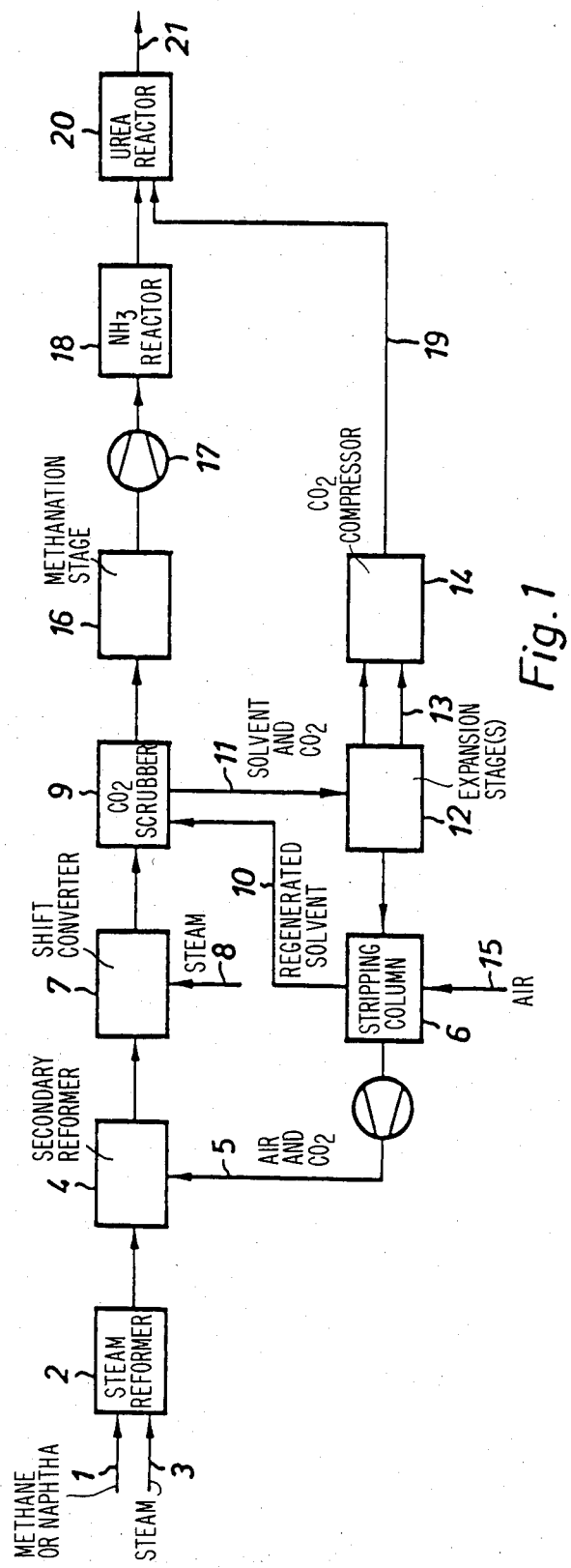
FIG. 1 is a block diagram for the integrated process.

As can be seen in the block diagram of FIG. 1, a gas containing a hydrocarbon, e.g., natural gas or naphtha, is fed by pipe 1 to a steam reformer 2 operated at a pressure of preferably 15 to 35 bar. In the latter, a catalytic reaction of the natural gas or naphtha occurs with the steam, brought in by pipe 3, to produce essentially $H_2+CO$. The methane in the hydrocarbon steam is, however, only partly reacted. The reformed gas is then passed to a secondary reformer (also called combustion chamber in the art, e.g., *Faith, Keyes & Clark's Industrial Chemicals*, 4th Edition, Lowenheim and Moran, Wiley & Sons, Inc., 1975, pp. 83-86) operated at a pressure of preferably about 14 to 34 bar. There, the residual methane in the gas leaving the steam reformer is reacted with air that is introduced by pipe 5. The amount of added air is sufficient to yield a mixture by moles of 3 $H_2+N_2$ required for ammonia synthesis. The $CO_2$ stripped in a stripping column 6 operated at preferably about 1, 1-2 bar, accompanies the air passed to the secondary reformer and is withdrawn from same without reaction.

The gas from the secondary reformer is then fed to a shift converter wherein the CO is reacted at preferably about 14 to 34 bar, with steam brought in by pipe 8, to $H_2$ and $CO_2$ according to the formula $$CO + H_2O = H_2 + CO_2$$

The residual CO content of the converted gas is still about 0.3%.

In a high pressure $CO_2$ scrubber 9 downstream from the shift converter, the $CO_2$ is removed at preferably about 15-70 bar, to a residual content of about 100 ppm of $CO_2$ with a physical solvent that is fed from stripping column 6 by pipe 10. The $CO_2$-loaded solvent is introduced via pipe 11, to an optionally multistage expansion stage 12 in which the $CO_2$ is degassed and fed by pipes 13 to a $CO_2$ compressor 14. The resultant partially regenerated solvent is fed to the stripping column 6 for further regeneration by the admission of air fed by pipe 15. The regenerated solvent is then returned by pipe 10 to the high pressure scrubber 9. The stripped residual $CO_2$ together with the air is fed by pipe 5 to secondary reformer 4.

The gas, largely freed of $CO_2$, in high pressure scrubber 9 is fed to a methanation stage 16 in which the CO and residual $CO_2$ is catalytically reacted with $H_2$ to form methane and water. After being compressed in gas compressor 17, and passed to reactor stage 18, ammonia is synthesized according to the reaction:

$$3H_2 + N_2 = 2NH_3$$

Finally, the compressed $CO_2$ fed from pipe 19 and the resultant ammonia from the reactor 18 are passed to a urea synthesis stage 20, in which $NH_3$ and $CO_2$ are converted to urea. The latter is removed by pipe 21.

Figure 2:
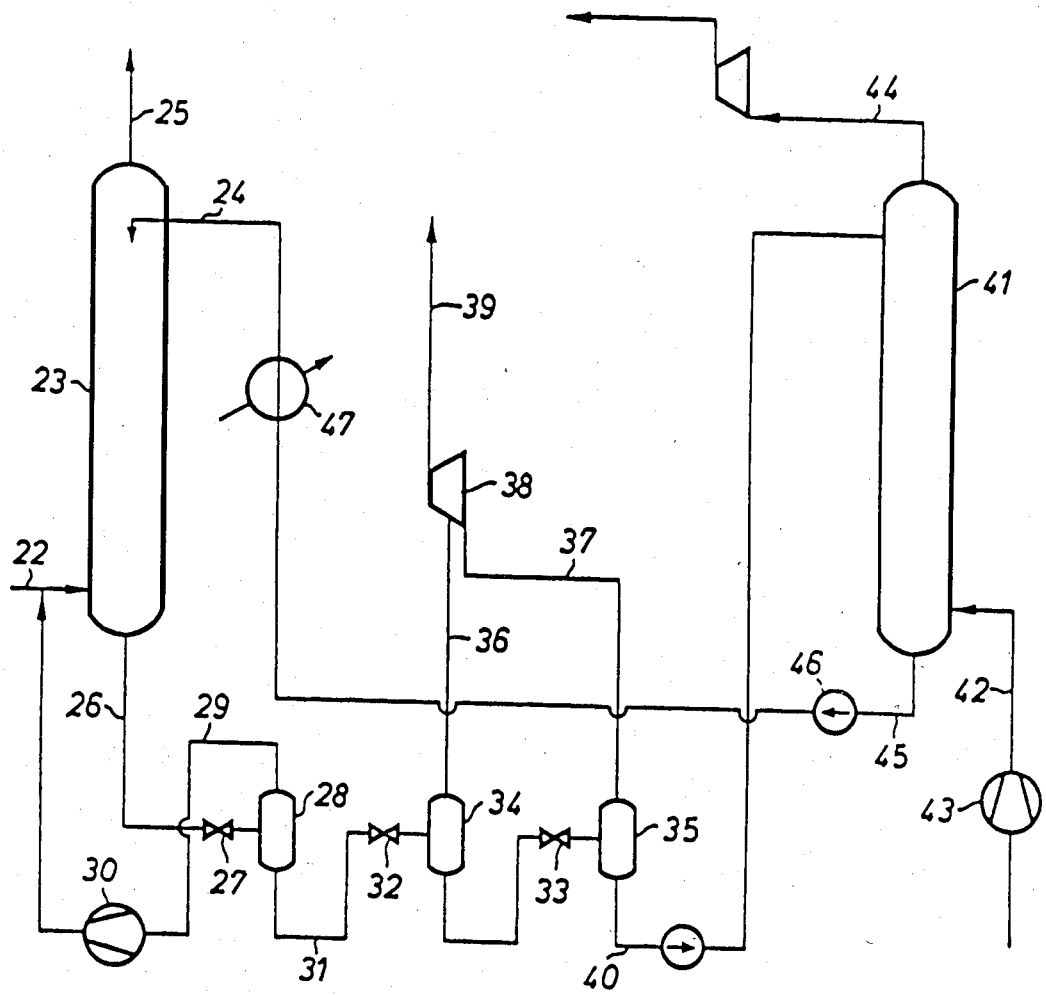
FIG. 2 is a detailed schematic flow sheet of a preferred comprehensive embodiment of the steps of scrubbing and regeneration.

The high pressure scrubbing and subsequent regeneration of the charged solvent is shown in FIG. 2. The gas coming in pipe 22 from shift converter 7 is scrubbed in a scrubbing column 23 with regenerated solvent that is fed to the column in the upper zone by pipe 24. In this step, the $CO_2$ is scrubbed to a residual content of about 100 ppm. The attainable purity is a function of the amount of solvent, temperature and the number of theoretical plates as manifested by actual plates or packing height.

Besides $CO_2$, other constituents of the crude gas are also absorbed in the solvent in accordance with the respective solubility of each constituent; at the same time water is also partially scrubbed out.

The gas removed from the top of scrubbing column 23 is fed to the methanation stage by pipe 25.

The charged solvent removed at the bottom of scrubbing column 26 is first pressure reduced to a pressure of preferably about 8-25 bar through a valve 27 into separator 28 and the gases, preferably $H_2$ and $N_2$, released thereby, are recycled to the scrubber by a pipe 29 by means of a recycle compressor 30. In this connection, this recycle compressor performs two tasks: increasing the $H_2$ yield and simultaneously increasing the $CO_2$ concentration for urea synthesis.

Thereafter, the solvent in pipe 31 is expanded step by step in valves 32, 33 into separators 34, 35. In this step, $CO_2$ is released in each case via pipes 36, 37 and is compressed with a $CO_2$ compressor 38 to the pressure of the urea synthesis and is fed to the latter by pipe 39. The number of expansion stages and compression stages are appropriately adjusted to one another.

After expansion to a pressure of about 1.3 bar, the solvent which still contains $CO_2$, is fed by pipe 40 to a stripping column 41 and there stripped with air fed by pipe 42 by means of compressor 43. At this point, the amount of air is so selected to convert the methane in the downstream secondary reformer and to provide the correct molar ratio for the ammonia synthesis gas mixture. With this amount of air, the $CO_2$ dissolved in the solvent is stripped and leaves stripping column 41 at the top by pipe 44.

The solvent removed at the bottom by pipe 45 is pumped to the pressure of the scrubbing column, 46. The heat associated with the crude gas and pumps is removed in a cooler 47.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE

Scrubbing and recovery of $CO_2$ from crude gas

The basis is a facility producing 1000 tons of $NH_3$ per day.

Process: the crude gas is compressed to 65 bar before scrubbing.

| | | | |
|---|---|---|---|
| Crude gas from the shift converter | | 6781.5 | kmol/h |
| Pressure | | 65 | bar |
| Composition | $H_2$ | 61.3 | mol % |
| | $N_2$ | 20.05 | mol % |
| | $CO + Ar + CH_4$ | 0.84 | mol % |
| | $CO_2$ | 17.81 | mol % |
| Product gas | | 5548.5 | kmol/h |
| Pressure | | 63.5 | bar |
| Composition | $H_2$ | 74.65 | mol % |
| | $N_2$ | 24.34 | mol % |
| | $CO + Ar + CH_4$ | 0.01 | mol % |
| | $CO_2$ | 100 | ppm |
| Scrubber | | | |
| Amount of solvent | | 800 | $m^3/h$ |
| | | of a polyethylene glycol ether | |
| Air as stripping gas | | 1718 | kmol/h |
| Recycling to secondary reformer | | 1916 | kmol/h |
| Pressure before compressor | | 1.3 | bar |
| Composition | Air | 89.5 | mol % |
| | $CO_2$ | 10.5 | mol % |
| $CO_2$-product | | | |
| Pressure | | 1.3 or 3 or 9 | bar |
| Composition | $H_2$ | 1.1 | mol % |
| | $N_2$ | 1.0 | mol % |
| | $CO + CH_4$ | 0.2 | mol % |
| | $CO_2$ | 97.7 | mol % |

The preceding example can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the combined production of ammonia and urea, comprising the steps of reacting gas containing hydrocarbons with steam in a steam reformer, reacting residual hydrocarbon in a downstream secondary reformer with air, reacting resultant CO in a shift converter to form $CO_2$ and $H_2$, scrubbing resultant ammonia synthesis gas consisting essentially of hydrogen, nitrogen and carbon dioxide with a physical solvent to remove $CO_2$, regenerating resultant $CO_2$-loaded physical solvent to recover a $CO_2$ stream, passing said $CO_2$ stream to urea synthesis, and recycling resultant regenerated solvent to the scrubbing step, the improvement wherein said regenerating of said physical solvent comprises: (a) effecting at least one pressure reduction step on the $CO_2$-loaded physical solvent to liberate a gaseous stream containing a major portion of the $CO_2$ for urea synthesis and to obtain a physical solvent having residual $CO_2$, and (b) stripping the latter residual $CO_2$-containing physical solvent with air as the stripping gas; recovering a mixture of the air together with said residual $CO_2$ from the stripping step and feeding said mixture into the secondary reformer.

2. A process according to claim 1, wherein said regenerating stage comprises, prior to said stripping, at least two pressure reduction steps, the first to degas CO and absorbed inert gases and the second to remove the major portion of the $CO_2$.

3. A process according to claim 1, wherein the crude gas is compressed before the scrubbing.

4. A process according to claim 1, wherein the regeneration final pressure is so selected that the amount of air needed for $CO_2$ stripping covers the requirement of the secondary reformer.

5. A process according to claim 4, further comprising subjecting resultant scrubbed ammonia synthesis gas to a methanation stage to remove residual CO and $CO_2$.

* * * * *